(12) United States Patent
Holland et al.

(10) Patent No.: US 9,950,855 B1
(45) Date of Patent: Apr. 24, 2018

(54) DISPENSER HAVING A SUB-ASSEMBLY FOR SELECTIVELY ENGAGING AND DISENGAGING A PLUNGER ROD

(71) Applicant: Neogen Corporation, Lansing, MI (US)

(72) Inventors: James Holland, Clinton, NC (US); Michael Benton, Hampstead, NC (US); Mitchell Rivenbark, Clinton, NC (US)

(73) Assignee: NEOGEN CORPORATION, Lansing, MI (US)

( * ) Notice: Subject to any disclaimer, the term of this patent is extended or adjusted under 35 U.S.C. 154(b) by 0 days.

(21) Appl. No.: 15/437,085

(22) Filed: Feb. 20, 2017

(51) Int. Cl.
| | |
|---|---|
| *B05C 17/01* | (2006.01) |
| *B65D 83/00* | (2006.01) |
| *B65D 47/06* | (2006.01) |
| *B05B 11/02* | (2006.01) |
| *A61D 7/00* | (2006.01) |
| *A61M 5/315* | (2006.01) |
| *A61M 5/20* | (2006.01) |

(52) U.S. Cl.
CPC ......... *B65D 83/0033* (2013.01); *B65D 47/06* (2013.01); *A61D 7/00* (2013.01); *A61M 5/204* (2013.01); *A61M 5/31583* (2013.01); *B05B 11/025* (2013.01); *B05C 17/01* (2013.01); *B05C 17/012* (2013.01); *B05C 17/0123* (2013.01)

(58) Field of Classification Search
CPC ... B05C 17/0123; B05C 17/01; B05C 17/012; B65D 83/0033; B65D 47/06; B05B 11/025; A61D 7/00; A61M 5/204; A61M 5/31583; A61M 5/31553
See application file for complete search history.

(56) References Cited

U.S. PATENT DOCUMENTS

| | | | |
|---|---|---|---|
| 1,930,929 A | * | 10/1933 | Eisenberg ............... A61M 5/31 604/183 |
| 2,316,095 A | | 4/1943 | Mead, Jr. |
| 2,695,023 A | | 11/1954 | Brown |
| 2,735,431 A | * | 2/1956 | Swanson ........... A61M 5/31595 604/223 |
| 3,141,583 A | | 7/1964 | Mapel et al. |
| 3,161,323 A | | 12/1964 | Bent |
| 3,248,950 A | | 5/1966 | Pursell et al. |
| 3,504,673 A | | 4/1970 | Parisi |
| 3,517,668 A | | 6/1970 | Brickson |
| 3,695,266 A | | 10/1972 | Lussier et al. |
| 4,022,207 A | | 5/1977 | Citrin |

(Continued)

FOREIGN PATENT DOCUMENTS

| | | |
|---|---|---|
| AU | 2016100772 A4 | 7/2016 |
| WO | 9826823 | 6/1998 |

OTHER PUBLICATIONS

Photograph of syringe believed to be from N.J. Phillips Pty. Ltd., Australia, and believed to be known or used before Dec. 2001 (6 pages).

(Continued)

*Primary Examiner* — Frederick C Nicolas
(74) *Attorney, Agent, or Firm* — Honigman Miller Schwartz and Cohn LLP; Douglas H. Siegel; Jonathan P. O'Brien (57) ABSTRACT

A dispenser including a sub-assembly to engage and disengage a plunger rod. The sub-assembly minimizes the need for springs and other biasing members within the dispenser.

22 Claims, 9 Drawing Sheets

(56) References Cited

U.S. PATENT DOCUMENTS

| | | | |
|---|---|---|---|
| 4,264,021 A * | 4/1981 | Davis, Jr. | B05C 17/012 |
| | | | 222/326 |
| 4,406,170 A | 9/1983 | Kuhn | |
| 4,444,560 A | 4/1984 | Jacklich | |
| 4,448,335 A | 5/1984 | Jessop | |
| 4,470,317 A | 9/1984 | Sabloewski et al. | |
| 4,632,669 A * | 12/1986 | Phipps, Sr. | A61M 25/1018 |
| | | | 604/118 |
| 4,659,327 A | 4/1987 | Bennett et al. | |
| 4,710,172 A | 12/1987 | Jacklich et al. | |
| 4,936,833 A | 6/1990 | Sams | |
| 4,974,752 A | 12/1990 | Sirek | |
| 4,994,065 A | 2/1991 | Gibbs et al. | |
| 5,046,642 A | 9/1991 | Cathcart et al. | |
| 5,336,183 A | 8/1994 | Greelis et al. | |
| 5,469,860 A | 11/1995 | De Santis | |
| 5,531,708 A | 7/1996 | Woodruff | |
| 5,733,258 A * | 3/1998 | Lane | A61M 5/31581 |
| | | | 604/209 |
| 5,755,362 A | 5/1998 | Rodriguez, Jr. et al. | |
| 5,816,452 A | 10/1998 | Woodruff | |
| 5,961,496 A | 10/1999 | Nielsen et al. | |
| 6,024,728 A | 2/2000 | Schulz | |
| 6,182,867 B1 | 2/2001 | Keller | |
| 6,286,729 B1 | 9/2001 | Lin | |
| 6,386,401 B1 * | 5/2002 | Dodd | B05C 17/01 |
| | | | 222/391 |
| 6,450,370 B2 | 9/2002 | Keller | |
| 7,341,574 B2 | 3/2008 | Schreijag | |
| 7,946,453 B2 * | 5/2011 | Voegele | A61B 17/00491 |
| | | | 222/134 |
| 2010/0168679 A1 | 7/2010 | Quinn et al. | |
| 2014/0291474 A1 | 10/2014 | Wilson et al. | |

OTHER PUBLICATIONS

Photograph of syringe believed to be from Henke-Sass, Wolf GmbH, Germany, and believed to be known or used before Dec. 2001. (2 pages).

International Search Report, PCT/EP03/02444, dated Oct. 3, 2003 (4 pages).

International Search Report and Written Opinion for PCT/US2017/018584 dated Dec. 21, 2017.

* cited by examiner

DISPENSER HAVING A SUB-ASSEMBLY FOR SELECTIVELY ENGAGING AND DISENGAGING A PLUNGER ROD

FIELD OF THE DISCLOSURE

This disclosure relates to a dispenser, and in particular, a dispenser having a sub-assembly configured to permit selective engagement and disengagement of the mechanisms to advance and retract the dispenser's plunger rod.

BACKGROUND

Common dispensers, such as a syringe dispenser, often include a barrel or tube for holding a material, fluid, medicine, or other medicament. The barrel or tube may have a needle or other injection member on one end and include a fitment on the other end for securing to the dispenser or dispenser body. The dispenser may include a piston within the barrel for dispensing the material out of the needle or other injection member. The piston is usually connected to a plunger rod that effects the advancement of the piston in the barrel.

Dispensers often include a mechanism to engage and disengage the plunger rod to lock or free the rod from movement. Such mechanisms in prior syringe dispensers commonly used multiple springs or multiple biasing members. Due to the stress on the multiple springs or biasing members in such systems, over time, these mechanisms may be less effective or prone to failure.

SUMMARY

According to one aspect, a dispenser including a body and having a longitudinal axis is described herein. The dispenser has a plunger rod extending into the body along the longitudinal axis and coupled thereto to permit advancement along and rotation about the longitudinal axis. The dispenser includes a handle operable to advance the plunger rod into the body and a sub-assembly including a ratchet and a cam member. The sub-assembly is in operative relation between the handle and the plunger rod and is configured to shift between an engagement and a disengagement of the handle with the plunger rod. The ratchet is biased into engagement with the plunger rod, and when the sub-assembly is engaged, effects forward advancement of the plunger rod along the longitudinal axis upon actuation of the handle. The cam member is coupled with the ratchet and the plunger rod and the cam member is positioned, upon rotation of the plunger rod about the longitudinal axis, to counter bias the ratchet away from the plunger rod to disengage the ratchet from the plunger rod and to permit rearward advancement of the plunger rod along the longitudinal axis.

In other aspects, the dispenser of the previous paragraph may further include other features either individually or in combination. For instance, the dispenser may further include a retainer housing of the sub-assembly where the retainer housing is coupled to both the handle and to the cam member, the retainer housing supports the ratchet; the retainer housing may define a yoke to rotatably receive at least a portion of the cam member therein; the cam member may be mounted to the plunger rod through a keyed relationship; the keyed relationship may include a D-shaped outer surface profile of the plunger rod and a corresponding D-shaped profile on a throughbore of the cam member; the cam member may include a cylindrical body defining a bore therethrough and with the plunger rod extending through the bore; the cam member may include a cylindrical body and may further include a camming lobe extending radially outward and circumferentially about the cam member body; the camming lobe may define a first camming surface extending a radial distance from the cam member body and a second camming surface extending a second radially farther distance from the cam member body; the second camming surface may be circumferentially spaced about 30 to about 60° from the first camming surface; the second camming surface of the camming lobe may be configured to counter bias the ratchet away from the plunger rod upon rotation of the plunger rod and the cam member about the longitudinal axis; the dispenser may have a needle mounted thereto; and/or the cam member may define a pair of stop surfaces proximate to the first and second camming surfaces.

In yet another aspect, a dispenser is described that includes a body defining a first and second end thereof and having a longitudinal axis extending between the ends. A barrel or tube may be mounted to the first end of the body with a plunger rod extending into the body from the second end and mounted for advancement along and for rotation about the longitudinal axis. The dispenser may further include a handle coupled to the plunger rod, a ratchet biased into engagement with the plunger rod, a ratchet retainer housing the ratchet and coupled to the handle; and a rotatable cam member mounted to the plunger rod and defining a cam surface positioned to counter bias the ratchet away from the plunger rod to disengage the handle from the plunger rod upon rotation thereof.

In other aspects, the dispenser of the previous paragraph may further include other features either individually or in combination. For instance, the ratchet retainer may define a yoke to rotatably receive a portion of the rotatable cam member therein; the rotatable cam member may be mounted to the plunger rod through a keyed relationship; the keyed relationship may include a D-shaped outer surface profile of the plunger rod and a corresponding D-shaped throughbore of the rotatable cam member; the rotatable cam member may include a cylindrical body defining a bore therethrough, the plunger rod extending through the bore; the rotatable cam member may include a cylindrical body and wherein the rotatable cam member further includes a camming lobe extending radially outward and circumferentially about the rotatable cam member body; the camming lobe may define a first camming surface extending a radial distance from the cam member body and a second camming surface extending a second radially farther distance from the rotatable cam member body, the second camming surface may be circumferentially spaced from the first camming surface; the second camming surface of the camming lobe may be configured to counter bias the ratchet away from the plunger rod upon rotation of the plunger rod and the rotatable cam member about the longitudinal axis; the dispenser may have a needled mounted thereto; and/or the cam member defines a pair of stop surfaces proximate to the first and second camming surfaces.

DETAILED DESCRIPTION

A dispenser is described herein. As discussed in the background, prior dispensers may include a locking feature to engage or disengage the dispenser plunger and associated plunger rod to either lock the rod or restrict movement to a single direction. Such prior locking features commonly included a biased ratchet-type member to engage the plunger rod and, in addition, a further spring-biased lock or other spring-loaded latching mechanism that engaged and locked the plunger rod. In such prior systems, mechanisms were employed to counter bias the lock or latch elements in order to unlock the plunger rod. The counter biasing feature of these prior lock or latch mechanisms may have been a momentary or a lockable feature. However, the added springs and other biasing elements of such prior locking mechanisms can wear out over time as the spring is stressed due to the repeated locking and unlocking of the plunger rod during use. This repeated stress can, in some instances, reduce the effectiveness of the lock and biasing elements thereof. The dispensers of the present disclosure, on the other hand, include a sub-assembly to engage and disengage the dispenser plunger rod without using additional biasing members and, thus, provides a more robust mechanism to engage and disengage the plunger rod during use.

The dispensers herein are suitable for medical or veterinary syringes or other uses in the medical or veterinary fields to dispense, withdraw, or inject fluids, liquids, gels, medicaments, and the like as needed for a particular application. The dispensers may also be used in other fields for dispensing or withdrawing materials as needed for use in such field. For example, the dispensers herein may also be used in the pest or insect management industry to dispense other fluids, liquids, gels, and the like appropriate for such use. For instance, the dispenser may be used with insecticides. In one approach, the barrel or tube of the dispenser may have a needle mounted to an end thereof to dispense or withdraw its materials. In other approaches, the dispenser or barrel of the dispenser may have other dispensing or withdrawing mechanisms mounted thereto, such as but not limited to, a sprayer, atomizer, or other nozzle-type assembly. For instance, the dispenser may have the nozzle assembly of U.S. application Ser. No. 12/186,980, which is incorporated herein by reference in its entirety, mounted thereto for dispensing materials.

Figure 1:
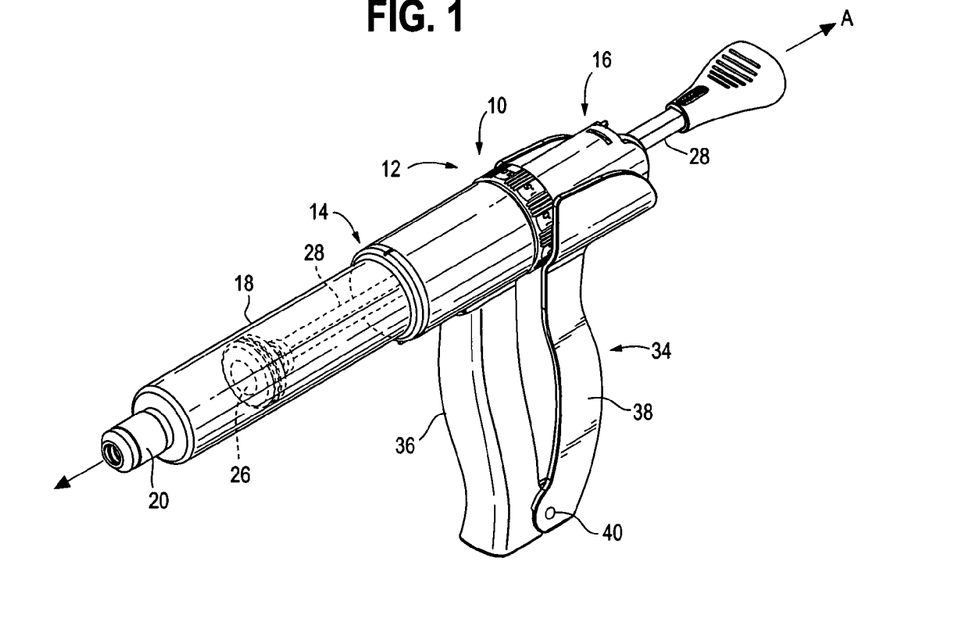
FIG. 1 is a perspective view of an exemplary dispenser.
Figure 2:
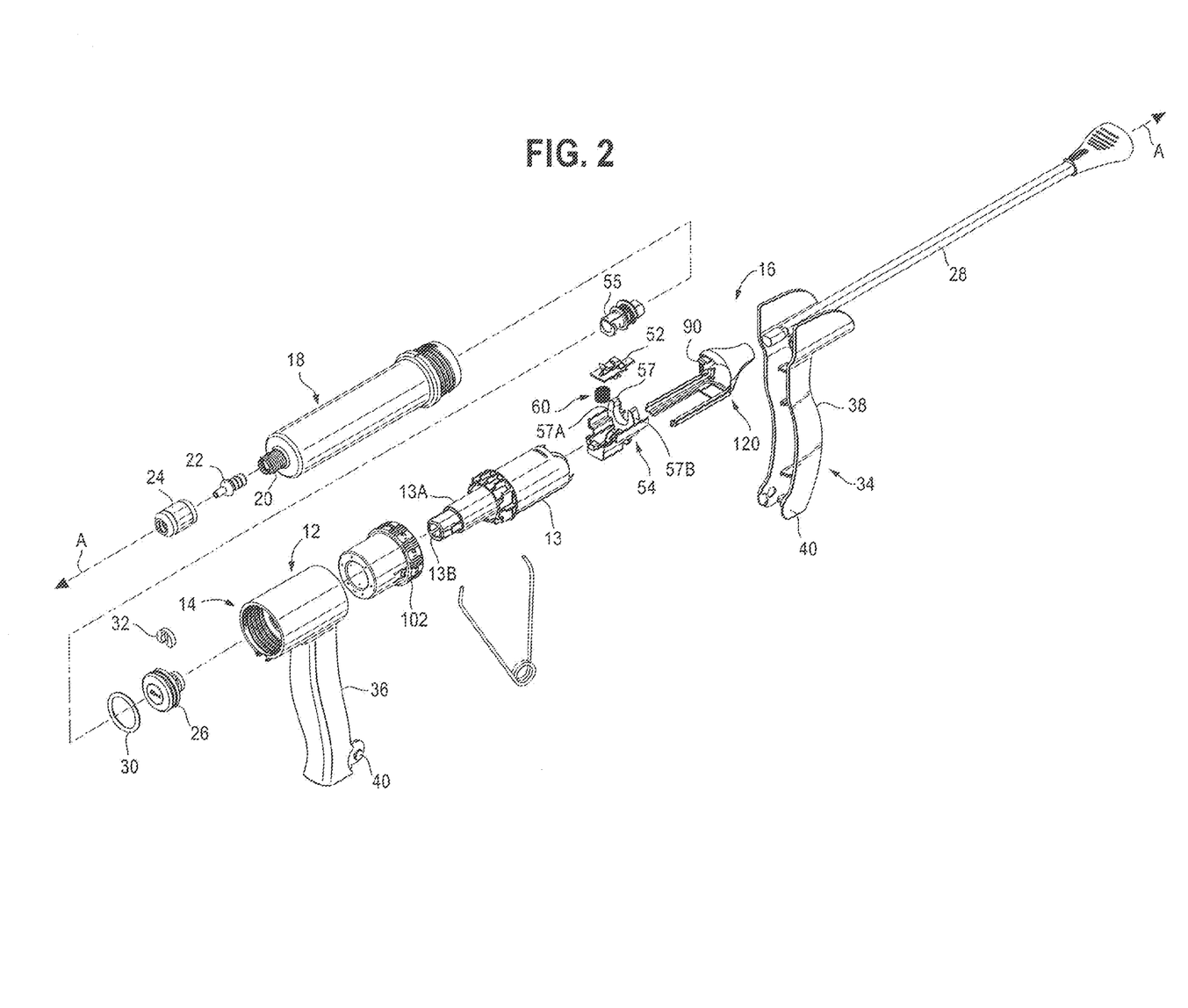
FIG. 2 is an exploded, perspective view of an exemplary dispenser.

Turning to more of the specifics, FIGS. 1 and 2 show an exemplary dispenser 10 including a dispenser body 12 with a first end 14 and a second end 16 and with a longitudinal axis A extending between the ends. Mounted directly or indirectly to the first end 14 of the dispenser body 12 is a barrel or tube 18 configured to receive a dispensable material, such as a fluid, gel, medicament, and the like. The dispenser barrel or tube 18 may include a distal end having a dispensing tip 20 upon which a needle nib or coupling 22 may be fastened. A needle (not shown) may be secured to the nib 22 using a needle nut or other coupling 24. The barrel or tube 18 may be directly mounted to the first end 14 of the dispenser body 12, for example, through a threaded engagement as generally shown in FIG. 2. The threaded engagement may be through external threading on the outer surface of the barrel 19 and corresponding internal threading on the inside of the dispenser body or vice versa. Alternatively, the barrel or tube 18 (or barrel or tube 204) may be indirectly mounted to the dispenser body 12 through an intermediate assembly or adapter mount as more fully discussed below with respect to FIGS. 8 and 9.

Figure 3:
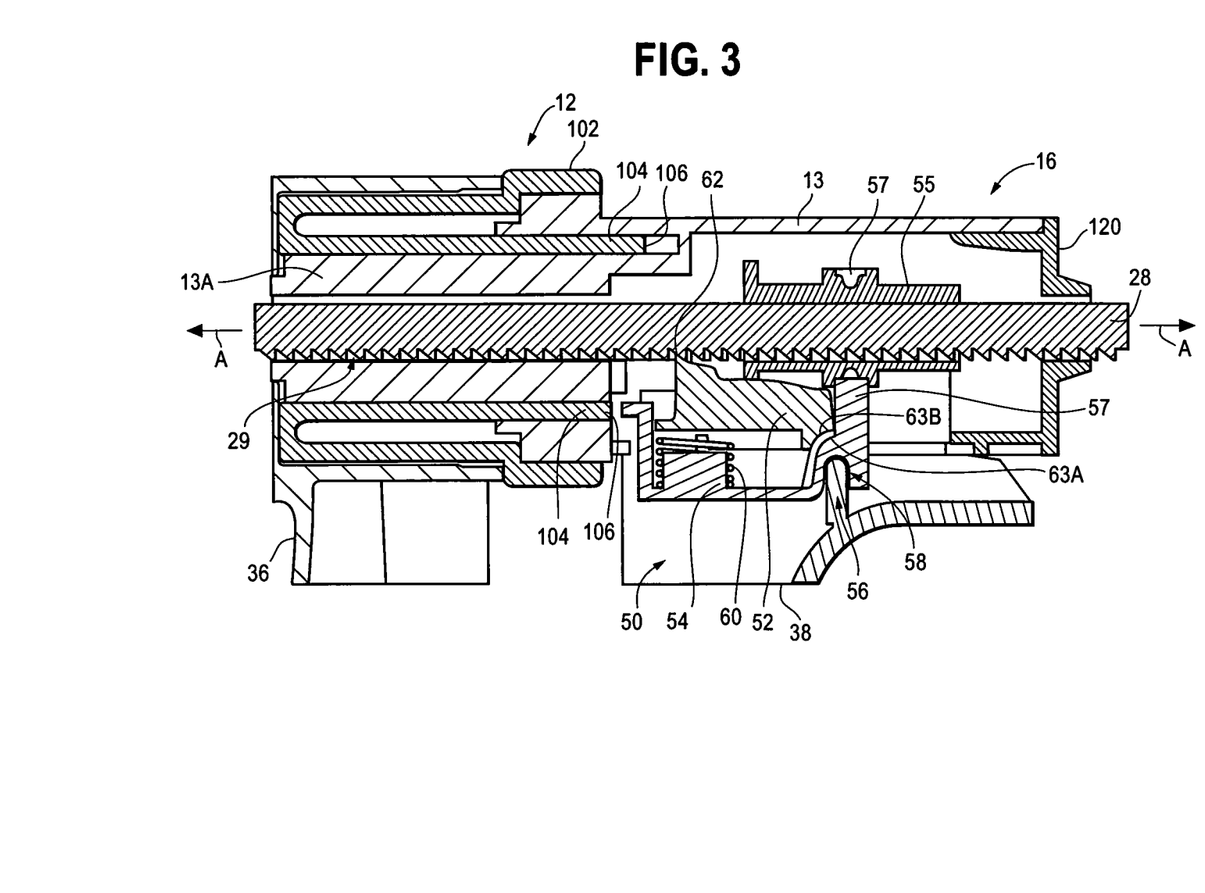
FIG. 3 is a cross-sectional view of a dispenser body.

The dispenser 10 may further include a piston 26 received within a cavity of the barrel or tube 18. The piston 26 is coupled to a plunger rod 28, which extends into the dispenser body 12 and is mounted thereto in a manner to permit advancement along and rotation about the longitudinal axis A. The plunger rod 28 is a shaft or other elongate member and, in one approach, defines a D-shaped outer profile having ratchet teeth or other serrations 29 on the curved surface of the D-shaped profile (FIG. 3). The flat portion of the rod 28 is free of any teeth or serrations. The piston 26 slides within the barrel cavity upon such longitudinal shifting or rotation of the plunger rod 28. The piston 26 may include a seal 30, such as an O-ring, and may be fastened to the distal end of the plunger rod via a snap ring 32. However, other types of sealing members and fastening features may be used as needed for a particular application.

The dispenser body 12 may further include an extension or plunger guide member 13, which may be a cylindrical guiding member having a projection 13A at a first end inserted within a portion of the dispenser body 12. The plunger guide 13 defines a bore or cavity 13B for receipt of the plunger rod 28 therethrough. The bore 13B aids in guiding the plunger rod 28 through the body 12 and into the barrel or tube 18.

The dispenser body 12 includes a handle 34, which is operable to advance the plunger rod 28 along the longitudinal axis A into the dispenser body 12 and barrel or tube 18. In one approach, the handle 34 is bifurcated into a front handle portion 36 and a rear handle portion 38 where each are pivotably connected 40 at a distal ends thereof. However, other arrangements of the handle 34 may be suitable and used as appropriate. As discussed further below, squeezing to pivot the rear handle portion 38 towards the front handle portion 36 moves a top end of the rear handle portion 38 forwardly and is operative to effect forward advancement of the plunger rod 28 and, thus, forward advancement of the piston 26 within the barrel or tube 18 to dispense any dispenser material from the barrel or tube. If needed, the dispenser 10 may also include a rear end cap or cover 120 (FIG. 2) that encloses or covers the inside of the dispenser body and the sub-assembly therein.

In one approach and turning to FIG. 3, the handle 34, and in particular the rear handle portion 38 may be operatively coupled to the plunger rod 28 through a sub-assembly 50. The sub-assembly 50 is a configured to switch between a first or engaged configuration with an operative engagement of the handle 34 to the plunger rod 28 and a second or disengaged configuration where the handle 34 is disengaged from the plunger rod 28. While the sub-assembly 50 can be any number of components to provide the operative connections and arrangements between the handle 34 and the plunger rod 28, in the approach as shown in FIG. 3 the sub-assembly 50 includes a ratchet 52, a retainer housing 54 in which the ratchet 52 is mountably received, a cam member 55 coupled with the ratchet 52 and the plunger rod 28, and a nib or other protrusion 56 defined on the upper end of the rear handle portion 38 where the nib 56 is coupled 58 to the retainer housing 54 (such as being received in a recess, notch, or other opening defined in the lower portion of the housing retainer 54). The collection of components within the sub-assembly 50 operatively interact to transfer advancement of the rear handle portion 38 into forward motion of the plunger rod 28 along the longitudinal axis A.

The ratchet 52 of the sub-assembly is pivotably mounted with or coupled to the retainer housing 54 at a rear end thereof. So mounted, the ratchet 52 is biased upwardly at the opposite or front end thereof, such as with a coil spring 60, so that a ratchet tooth (or ratchet teeth) 62 of the ratchet 52 engages one of the plunger rod teeth or serrations 29 of the rod 28 when the sub-assembly is in its engagement configuration as generally shown in FIG. 3 (and the rod 28 is turned so that the teeth 29 are facing the ratchet 52). The pivotable mounting or coupling between the ratchet 52 and the retainer housing 54 may include a curved shoulder 63A defined in ratchet seat of the housing 54 and a corresponding curved base 63B on the lower, rear end of the ratchet 52 to permit a sliding and/or pivoting interface therebetween. The mounting of the ratchet 52 within the sub-assembly 50 may be achieved through other mounting methods as needed for a particular application.

The retainer housing 54 further defines a yoke 57 (FIG. 2 and FIG. 3) at a rear end thereof through a pair of arcuate yoke arms 57A and 57B. The yoke 57 is configured to rotatably receive at least a portion of the cam member 55 therein and permits the cam member 55 to rotate about the axis A.

When the dispenser 12 and sub-assembly 50 thereof is arranged in the engaged configuration (FIG. 3 and FIG. 6A), the spring 60 biases the ratchet 52 upwardly so that the ratchet tooth 62 engages one of the plunger rod serrations 29. In this configuration, squeezing or moving the rear handle portion 38 toward the front handle portion 36 drives the protrusion 56 forwardly. The protrusion 56, being in engagement with the retainer housing 54, then drives the retainer housing 54 forwardly along the longitudinal axis A. The movement of the retainer housing 54 then translates the ratchet 52 forwardly along the axis A, and because the ratchet is engaged with the plunger rod 28, the plunger rod 28 is shifted or translated forwardly along the longitudinal axis A to move the piston 26 within the barrel or tube 18.

Figure 6A:
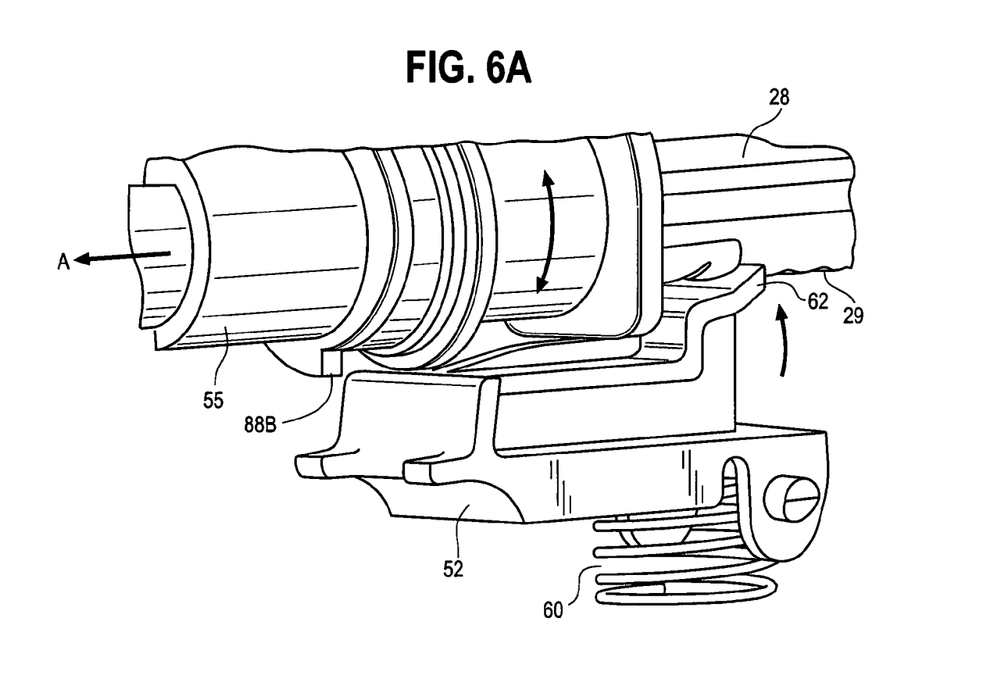
FIGS. 6A and 6B are perspective views of an exemplary cam member and exemplary ratchet.
Figure 6B:
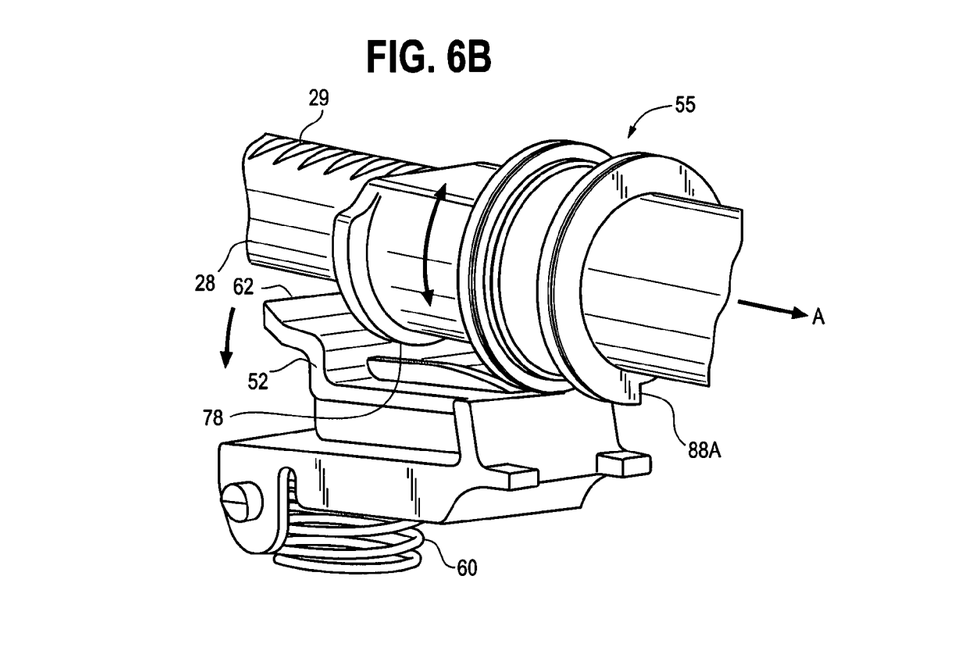

As generally shown in FIGS. 6A and 6B, portions of the sub-assembly 50 are illustrated to show engagement (FIG. 6A) and disengagement (FIG. 6B) of the ratchet 52 with plunger rod 28 in response to the cam member 55. In one approach and discussed more below, to disengage the sub-assembly 50 from the plunger rod 28, the cam member 55 is rotated about the longitudinal axis A to cam the ratchet 52 downwardly and away from the plunger rod 28 (FIG. 6B). Because of a keyed engagement between the cam member 55 and plunger rod 28, which is discussed further below, the cam member 55 may be rotated by turning the plunger rod 28 about the longitudinal axis A. Upon turning the cam member 55 to a disengaged rotary position, the ratchet tooth 62 is separated from the plunger rod serrations 29 to thereby free the plunger rod 28 from any connections or mating with the sub-assembly 50 (FIG. 6B). In this configuration, a user is free to pull back (or push forward) on the plunger rod to retract the piston 26 in a rearwardly (or advance in a forwardly) direction in the barrel or tube. The user can push or pull the distal end of the rod.

Turning back to FIGS. 4 and 5, further details of an exemplary cam member 55 of the sub-assembly are shown. In one approach, the cam member 55 is a generally cylindrical body 70 defining a bore 72 therethrough for receipt of the plunger rod 28. As noted above, the cam member 55 and plunger rod 28 have a keyed relationship to hinder or prevent relative rotational movement therebetween. In one approach, the keyed relationship includes the D-shaped outer surface profile on the plunger rod and a corresponding D-shaped inner profile on the throughbore 72 of the cam member 55. While the keyed relationship hinders relative rotational movement between the cam member 55 and plunger rod 28, the bore 72 is also sized to permit longitudinal sliding of the plunger rod 28 through the bore 72 during operation of the dispenser as described herein.

Figure 4:
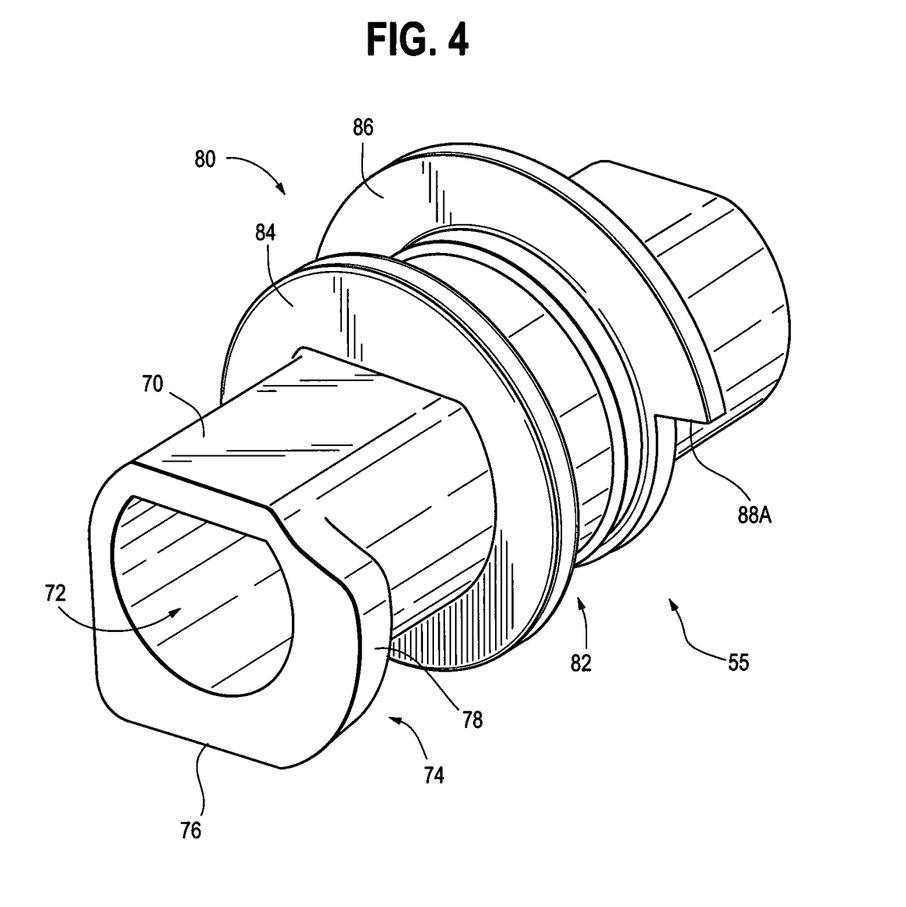
FIG. 4 is a perspective view of an exemplary cam member of the dispensers described herein.
Figure 5:
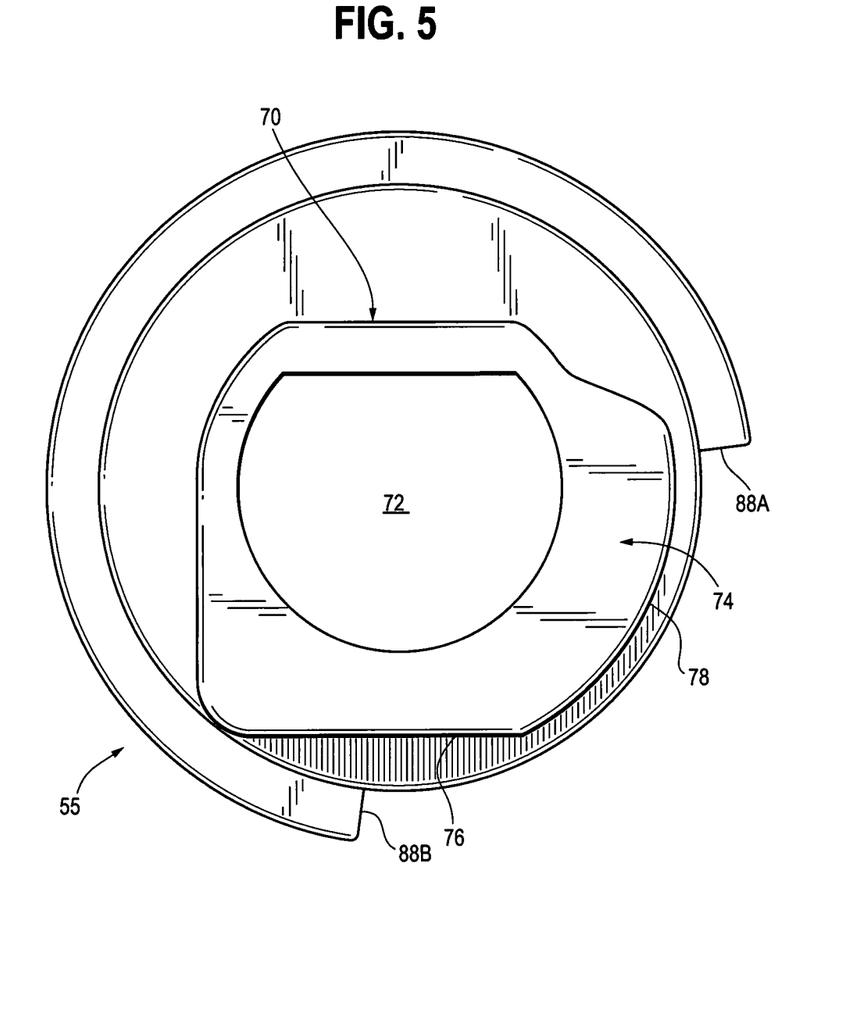
FIG. 5 is a plan view of the cam member of FIG. 4.

The cam member 55 further includes a cam lobe 74 extending radially outward and circumferentially about the cam member body 70. The cam lobe 74 includes a first camming surface 76 extending a short radial distance from the cam member body 70 and a second camming surface 78 of the lobe extending a second radially further distance from the cam member body 70. In one approach, the second cam surface 78 is about 30 to about 60° from the first cam surface 76.

The first cam surface 76 is arranged so that when the cam member 55 is rotated to position the surface 76 adjacent the ratchet 52, the first cam surface 76 is either spaced from the ratchet 52 or contacts the ratchet in a manner to not counteract the upwardly biasing force of the spring 60 (that is, FIGS. 3 and 6A). So configured, the cam member 55 and surface 76 thereof then permits the ratchet 52 to engage to plunger rod 28 as discussed above. Upon turning the cam member 55 (due to the keyed relationship with the plunger rod 28, by simply turning or rotating the plunger rod 28 about the A axis), the cam member 55 can be rotated to a position in which the second cam surface 78 engages the ratchet 52 to thereby cam or pivot the ratchet 52 downwardly away from the plunger rod 28 as shown in FIG. 6B. In this configuration, the cam member 55 is positioned to free the sub-assembly 50 and ratchet 52 thereof from its engagement with the plunger rod 28. In this disengaged configuration, the plunger rod 28 is then free to shift or translate in either a forward or rearward direction upon pushing or pulling an end of the rod; thus, the plunger rod 28 can move independent of the handle 34, 36, or 38. The cam member 55 may intermittently engage the ratchet 52 such as when the cam surface 78 engages and cams the ratchet in the disengaged configuration, and in the engaged configuration with the other cam surface 76 spaced from the ratchet. Alternatively, both the cam surfaces 76 and 78 may engage the ratchet with each engagement arranged to cam or not cam the ratchet to achieve the desired engagement or disengagement as discussed herein.

The cam member 55 further includes a pair of spaced circumferential fins 84, 86 that define a channel 82 therebetween. The channel 82 receives the yoke arms 57A and 57B of the yoke 57 of the retainer housing 54 and permits the cam member 55 to rotate about the longitudinal axis A relative to the yoke arms. In one approach, the yoke arms 57A and 57B are resilient and flex to allow the cam to snap into receipt thereof. One of the fins 86 includes a pair of stop surfaces 88A and 88B that correspond to each of the camming surfaces 76 and 78 on the cam lobe 74. For instance, one stop surface 88B corresponds with the first cam surface 76 and the second stop surface 88A corresponds with the second cam surface 78. Each of the cam fin stop surfaces 88A and 88B are configured to engage a positive stop 90 (FIG. 2) within the dispenser body 12 upon rotation of the cam member 55 to provide a tactile indication to a user that upon rotation of the cam (and plunger) the user has selected and positioned the cam 55 in either the engaged or disengaged configuration of the sub-assembly. While the positive stop 90 is shown on the end cap 120, it may be positioned on other components or as needed in the dispenser body.

The dispenser 12 may also include a dosing mechanism 100 that provides a set dose amount to be dispensed each time the handle 34 is operated or squeezed. FIGS. 2, 3, 7A, and 7B illustrate one approach of an exemplary dosing mechanism 100. For instance, the dosing mechanism 100 may include a rotary dial 102 that is mounted for rotation to the dispenser body 12, such as by rotation about the plunger guide 13 (or about the plunger guide extension 13A thereof). The rotary dial 102 may include a collar 104 defining a series of circumferential positive stop surfaces 106 that are each circumferentially spaced on an outer edge of the collar 104 a different axial distance X along the longitudinal axis A.

Figure 7A:
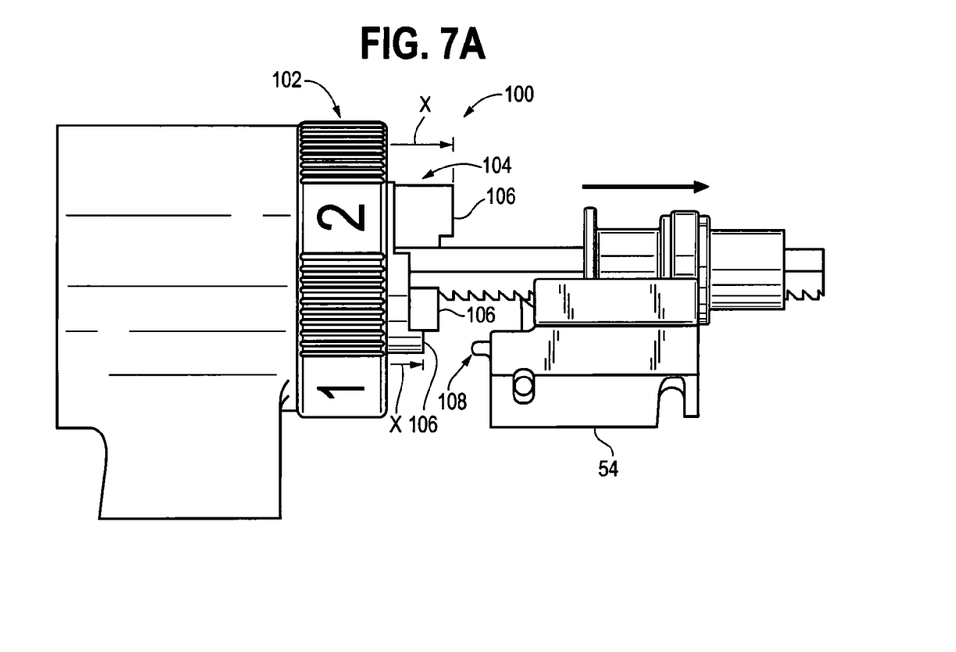
FIGS. 7A and 7B are side views of an exemplary dosing mechanism for the dispensers described herein.
Figure 7B:
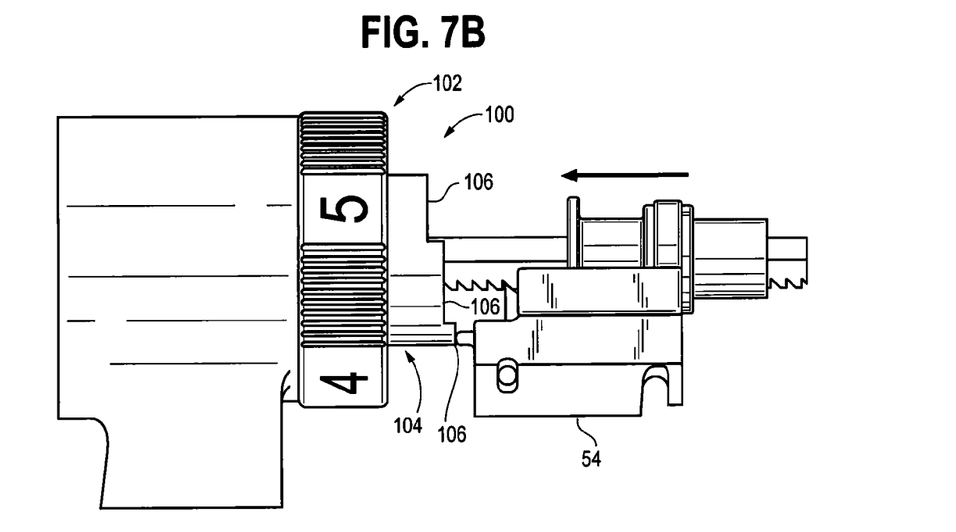

As shown in FIGS. 7A and 7B, the retainer housing 54 defines a forward stop flange 108 that is positioned to engage one of the selected circumferential positive stop surfaces 106 upon actuation of the handle 34. The distance between a forward surface of the retainer stop flange 108 and the selected circumferential stop surface 106 of the rotary dial defines a travel distance of the dispenser handle. The travel distance corresponds to a selected dose for each handle actuation. As appreciated, if the rotary dial 102 is rotated to select to a circumferential positive stop 106 with a short distance X, then upon actuation of the handle 34 the retainer housing 54 may move a long travel distance corresponding to a large dose. If the rotary dial 102 is rotated to select a circumferential positive stop 106 with a larger distance X, then upon actuation of the handle 34, the retainer housing 54 may move a shorter travel distance corresponding to a smaller dose. Of course, the rotary dial 102 may define a number of positive stops 106 with varying stop distances X so that the collar 104 includes an outer peripheral edge having an annular, stair-stepped profile.

Figure 8:
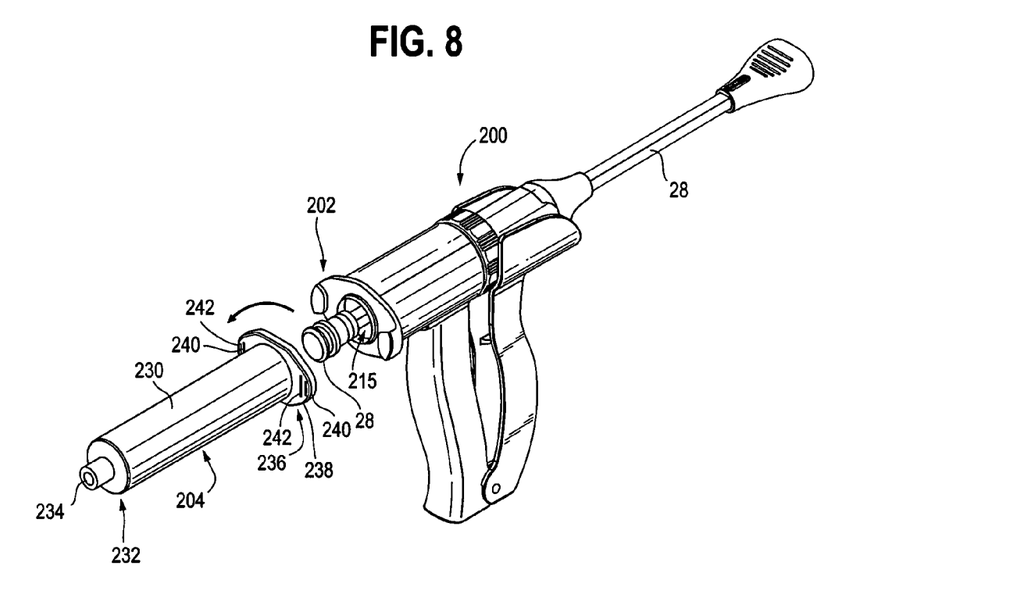
FIG. 8 is an exploded, perspective view of an exemplary dispenser with an adapter mount for a barrel or tube.
Figure 9:
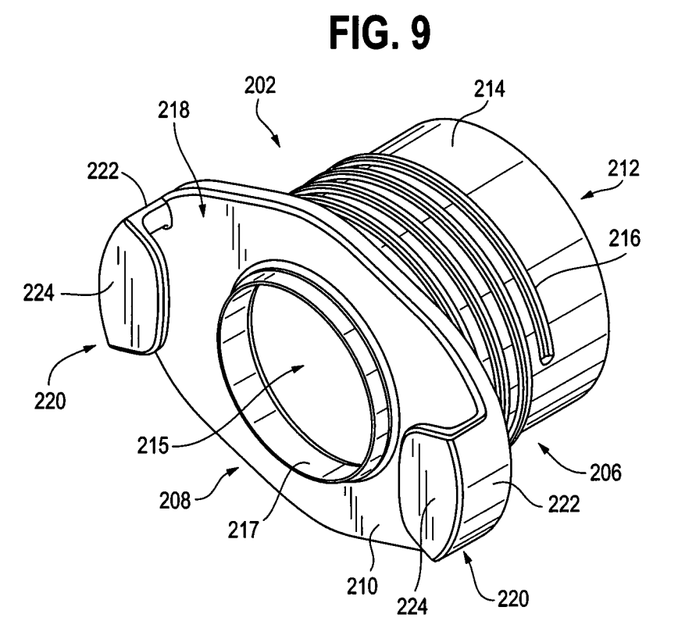
FIG. 9 is a perspective view of an exemplary adapter mount.

Turning to FIGS. 8 and 9, a dispenser and adapter mount therefor is illustrated to indirectly mount a barrel or tube to the dispenser body. In one approach, a dispenser 200 is illustrated with an adapter mount 202 for releasably and indirectly mounting a dispenser barrel or other tube 204 thereto. By one approach, the dispenser 200 may be the dispenser 10 discussed above and the barrel 204 may be barrel or tube 18 or a modified version of the barrel or tube 18.

The adapter mount 202 is receivable in the first end 14 of the dispenser 200 and provides an interface to easily mount the barrel 18 or 204 thereto. By one approach, the adapter mount 202 is threadably mounted to or received in the dispenser first end 14 and includes an outer threaded portion configured to threadably mate with an inner threaded portion on the dispenser first end 14 (this threading configuration may also be reversed as needed for a particular application).

More specifically and as best shown in FIG. 9, the adapter mount 202 includes a body 206 having a first end 208 including a faceplate 210 configured to mount and receive the barrel or tube 204 and a second end 212 configured to be mounted to or received in the dispenser body 12. As shown, the second end 212 is an annular extension 214 out from the faceplate 210 and defines outer threading 216. The adapter mount 202 defines a throughbore 215 through the faceplate and the annular extension thereof. The faceplate 210 may define an outwardly extending annular flange or rim 217 encircling the throughbore 215 and extending outwardly therefrom. The rim 217 is configured to seat within the barrel 204 and form a seal therewith. As shown in FIG. 8, when mounted, the plunger 28 and piston 26 may extend through the adapter mount throughbore 215 to interface with the tube or barrel 204 and/or any associated piston or the like therein.

By one approach, the faceplate 210 is an elongate member defining a mount 218 for the barrel or tube 204 in the form of, for example, a latch mount, snap-on mount, bayonet mount, quick-release mount, and the like. Other mounting methods may be used as needed for a particular application or circumstance. As shown, the mount 218 is a rotatable latch-type mount with opposing flanges 220 on opposite sides of the faceplate 210. Each flange 220 is a generally dog-leg or L-shaped arm that extends outwardly from the baseplate 210 and each includes a side arm 222 and a top, inwardly extending flange 224.

In the approach shown in FIG. 8, the barrel or tube 204 may include a tubular body 230 having a dispensing end 232 with a barrel outlet 234 and an opposite mounting end 236 configured for mounting to the adapter mount 202. As shown, the mounting end 236 includes a barrel baseplate 238 in the form on an elongate member having finger extensions 240 on opposite sides thereof. The finger extensions 240 may include nubs, bossing, ridges, and the like 242 on an upper surface thereof. The finger extensions 240 are sized to be frictionally received within the space between the top, inwardly extending flange 224 of the dog-leg extensions and the upper surface of the faceplate 210 on the adapter mount 202. For example, to mount the barrel 204 to the dispenser body 12, the elongate barrel baseplate 238 is positioned generally transverse or generally crosswise to the adapter mount face plate 210 so that the finger extensions 240 are spaced, such as in a radial direction, from the flanges 220. The barrel or tube 204 is then turned (such as by about 90°) so that the finger extensions 240 are then frictionally received with an interference fit under the top, inwardly extending flanges 224 to securely fasten the barrel 204 to the mount 202 and dispenser end 14. The dispenser can then be used as previously described to dispense a material from the barrel or tube 204.

The illustrative embodiments have been described hereinabove. It will be apparent to those skilled in the art that the above compositions and methods may incorporate changes and modifications without departing from the general scope of this disclosure. It is intended to include all such modifications and alterations within the scope of the present disclosure. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A dispenser comprising:
   a body having a longitudinal axis;
   a plunger rod extending into the body along the longitudinal axis and coupled thereto to permit advancement along and rotation about the longitudinal axis;
   a handle operable to advance the plunger rod into the body;
   a sub-assembly including a ratchet and a cam member;
   wherein the sub-assembly is in operative relation between the handle and the plunger rod and the sub-assembly is configured to shift between an engagement and a disengagement of the handle with the plunger rod;
   wherein the ratchet is biased into engagement with the plunger rod, when the sub-assembly is engaged, to effect forward advancement of the plunger rod along the longitudinal axis upon actuation of the handle; and
   wherein the cam member is coupled with the ratchet and the plunger rod and the cam member is positioned, upon rotation of the plunger rod about the longitudinal axis, to counter bias the ratchet away from the plunger rod to disengage the ratchet from the plunger rod and to permit rearward advancement of the plunger rod along the longitudinal axis.

2. The dispenser of claim 1, further comprising a retainer housing of the sub-assembly and coupled to both the handle and to the cam member, the retainer housing supporting the ratchet.

3. The dispenser of claim 2, wherein the retainer housing defines a yoke to rotatably receive at least a portion of the cam member therein.

4. The dispenser of claim 1, wherein the cam member is mounted to the plunger rod through a keyed relationship.

5. The dispenser of claim 4, wherein the keyed relationship includes a D-shaped outer surface profile of the plunger rod and a corresponding D-shaped profile on a throughbore of the cam member.

6. The dispenser of claim 1, wherein the cam member includes a cylindrical body defining a bore therethrough, the plunger rod extending through the bore.

7. The dispenser of claim 1, wherein the cam member includes a cylindrical body and further includes a camming lobe extending radially outward and circumferentially about the cam member body.

8. The dispenser of claim 7, wherein the camming lobe defines a first camming surface extending a radial distance from the cam member body and a second camming surface extending a second radially farther distance from the cam member body.

9. The dispenser of claim 8, wherein the second camming surface is circumferentially spaced about 30 to about 60° from the first camming surface.

10. The dispenser of claim 8, wherein the second camming surface of the camming lobe is configured to counter bias the ratchet away from the plunger rod upon rotation of the plunger rod and the cam member about the longitudinal axis.

11. The dispenser of claim 7, wherein the cam member defines a pair of stop surfaces proximate to the first and second camming surfaces.

12. The dispenser of claim 1, further including a needle mounted to the body.

13. A dispenser comprising:
a dispenser body defining a first and second end thereof and having a longitudinal axis extending between the first and second ends;
a barrel mounted to the first end of the dispenser body;
a plunger rod extending into the dispenser body from the second end and mounted for advancement along and for rotation about the longitudinal axis;
a handle coupled to the plunger rod;
a ratchet biased into engagement with the plunger rod;
a ratchet retainer housing the ratchet and coupled to the handle; and
a rotatable cam member mounted to the plunger rod and defining a cam surface positioned to counter bias the ratchet away from the plunger rod to disengage the handle from the plunger rod upon rotation thereof.

14. The dispenser of claim 13, wherein the ratchet retainer defines a yoke to rotatably receive a portion of the rotatable cam member therein.

15. The dispenser of claim 13, wherein the rotatable cam member is mounted to the plunger rod through a keyed relationship.

16. The dispenser of claim 15, wherein the keyed relationship includes a D-shaped outer surface profile of the plunger rod and a corresponding D-shaped throughbore of the rotatable cam member.

17. The dispenser of claim 13, wherein the rotatable cam member includes a cylindrical body defining a bore therethrough, the plunger rod extending through the bore.

18. The dispenser of claim 17, wherein the rotatable cam member includes a cylindrical body and wherein the rotatable cam member further includes a camming lobe extending radially outward and circumferentially about the rotatable cam member body.

19. The dispenser of claim 18, wherein the camming lobe defines a first camming surface extending a radial distance from the cam member body at one end thereof and a second camming surface extending a second radially farther distance from the rotatable cam member body, the second camming surface circumferentially spaced from the first camming surface.

20. The dispenser of claim 19, wherein the second camming surface of the camming lobe is configured to counter bias the ratchet away from the plunger rod upon rotation of the plunger rod and the rotatable cam member about the longitudinal axis.

21. The dispenser of claim 18, wherein the cam member defines a pair of stop surfaces proximate to the first and second camming surfaces.

22. The dispenser of claim 13, further including a needle mounted to an end of the barrel.

* * * * *

UNITED STATES PATENT AND TRADEMARK OFFICE
CERTIFICATE OF CORRECTION

PATENT NO. : 9,950,855 B1
APPLICATION NO. : 15/437085
DATED : April 24, 2018
INVENTOR(S) : James B. Holland et al.

Page 1 of 1

It is certified that error appears in the above-identified patent and that said Letters Patent is hereby corrected as shown below:

In the Claims

In Claim 11, at Column 9, Line 39, the claim dependency is currently on claim 7 but should be on claim 8.

In Claim 21, at Column 10, Line 42, the claim dependency is currently on claim 18 but should be on claim 19.

Signed and Sealed this
Twenty-seventh Day of August, 2019

Andrei Iancu
*Director of the United States Patent and Trademark Office*